United States Patent
Patel et al.

(10) Patent No.: US 11,628,136 B2
(45) Date of Patent: Apr. 18, 2023

(54) ORAL CARE COMPOSITIONS COMPRISING AT LEAST ONE PHOSPHATE/ACRYLATE COPOLYMER AND AT LEAST ONE CATIONIC ACTIVE INGREDIENT

(71) Applicant: Colgate-Palmolive Company, New York, NY (US)

(72) Inventors: Vyoma Patel, Hillsborough, NJ (US); Rensl Dillon, Ewing, NJ (US); Shira Pilch, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 510 days.

(21) Appl. No.: 16/062,151

(22) PCT Filed: Dec. 16, 2016

(86) PCT No.: PCT/US2016/067347
§ 371 (c)(1),
(2) Date: Jun. 14, 2018

(87) PCT Pub. No.: WO2017/106763
PCT Pub. Date: Jun. 22, 2017

(65) Prior Publication Data
US 2018/0369122 A1    Dec. 27, 2018

Related U.S. Application Data

(60) Provisional application No. 62/268,925, filed on Dec. 17, 2015.

(51) Int. Cl.
| | | |
|---|---|---|
| *A61K 8/81* | (2006.01) | |
| *A61Q 11/00* | (2006.01) | |
| *A61K 8/365* | (2006.01) | |
| *A61K 8/90* | (2006.01) | |
| *A61K 8/27* | (2006.01) | |
| *A61Q 17/00* | (2006.01) | |
| *A61K 8/49* | (2006.01) | |
| *A61K 8/41* | (2006.01) | |

(52) U.S. Cl.
CPC .............. *A61K 8/8152* (2013.01); *A61K 8/27* (2013.01); *A61K 8/365* (2013.01); *A61K 8/416* (2013.01); *A61K 8/4926* (2013.01); *A61K 8/8164* (2013.01); *A61K 8/90* (2013.01); *A61Q 11/00* (2013.01); *A61Q 17/005* (2013.01); *A61K 2800/74* (2013.01)

(58) Field of Classification Search
CPC ........ A61K 8/27; A61K 8/416; A61K 8/8152; A61K 8/8164; A61K 8/365; A61K 8/90; A61Q 11/00
See application file for complete search history.

(56) References Cited

U.S. PATENT DOCUMENTS

| | | | |
|---|---|---|---|
| 3,937,807 A * | 2/1976 | Haefele | A61K 8/43 |
| | | | 424/52 |
| 5,292,526 A | 3/1994 | Gaffar et al. | |
| 9,801,795 B2 | 10/2017 | Nesta et al. | |
| 9,931,291 B2 | 4/2018 | Prencipe et al. | |
| 2007/0025928 A1 | 2/2007 | Glandorf et al. | |
| 2007/0053849 A1 | 3/2007 | Doyle et al. | |
| 2012/0034280 A1 | 2/2012 | Cohen et al. | |
| 2015/0087582 A1 | 3/2015 | Lovetri et al. | |
| 2016/0331667 A1 | 11/2016 | Nesta et al. | |
| 2016/0331668 A1 | 11/2016 | Zaidel | |
| 2016/0331670 A1 | 11/2016 | Prencipe et al. | |

FOREIGN PATENT DOCUMENTS

| | | |
|---|---|---|
| WO | WO 2015/094332 | 6/2015 |
| WO | WO 2015/094336 | 6/2015 |

OTHER PUBLICATIONS

International Search Report and Written Opinion of Corresponding Application No. PCT/US2016/067347, dated Mar. 9, 2017. WO. Dentaid2013, "Gingival Mouthwash", Database GNPD MINTEL, AN 2191385.

* cited by examiner

*Primary Examiner — Lezah Roberts*

(57) ABSTRACT

Disclosed herein are oral care compositions comprising at least one phosphate/acrylate copolymer, at least one cationic antibacterial agent, at least one synthetic anionic linear polycarboxylate polymer, at least one surfactant, and zinc lactate. Also disclosed herein are methods for the treatment and/or inhibition of gum disease or halitosis comprising contacting the oral cavity with the oral care compositions disclosed herein, as well as methods of making the oral care compositions disclose herein.

13 Claims, No Drawings

ORAL CARE COMPOSITIONS COMPRISING AT LEAST ONE PHOSPHATE/ACRYLATE COPOLYMER AND AT LEAST ONE CATIONIC ACTIVE INGREDIENT

Cross Reference to Related Applications

This application is a United States Application under 35 U.S.C. 371 claiming benefit of PCT Application No. PCT/US2016/067347, filed on Dec. 16, 2016, which claims the benefit of U.S. Provisional Application No. 62/268,925, filed on Dec. 17, 2015.

BACKGROUND

Dental plaque or plaque bio-film is a soft deposit that forms on teeth and is implicated in the occurrence of gingivitis and other forms of periodontal disease. Various cationic antibacterial agents have been found to have the clinical ability to retard the growth of bacteria and hence have the ability to minimize plaque formation, oral infections and dental disease associated therewith. Many cationic active ingredients are theorized to have antimicrobial action due to their ability to bind to negatively-charged protein moieties on bacterial cells present in the mouth. For example, cetyl pyridinium chloride (CPC) is believed to function in this manner and is regarded as an effective antibacterial/antiplaque active ingredient for oral compositions. Other cationic actives are theorized to function as anti-attachment compounds that prevent attachment of bacteria to enamel tooth surfaces by modifying the surface energy of the enamel. Such actives include antibacterial amino acid derivative esters, such as ethyl lauroyl arginine. Accordingly, the efficacy of a cationic active ingredient's function may be dependent upon preserving its cationic properties in vivo to prevent the formation of plaque, gingivitis, and cavities.

There are difficulties, however, associated with providing a stable oral care composition that preserves the cationic nature of the cationic active ingredients, their bioavailability and their efficacy. This is particularly difficult because many conventional oral care ingredients, such as inorganic particulate abrasives and surfactants, have an anionic (negative) nature. Cationic active ingredients are potentially attracted and bound to such negatively-charged ingredients, and hence are prevented from performing their intended function. Although the cationic active material ingredients, such as for example, antibacterial amino acid ester compounds, are effective antibacterial agents in vitro, these ingredients have often been observed not to exhibit the desired efficacy when applied in vivo by oral composition. Moreover, many oral care compositions, such as mouthwashes, may have a high water content. A high water content fosters the growth of bacteria in an oral care composition, and consequently shortens the shelf-life of the composition, resulting in consumer dissatisfaction.

Accordingly, it is desirable to formulate oral care compositions, such as mouthwashes, comprising cationic active ingredients together with anionic ingredients, wherein the compositions remain stable over their shelf life while maintaining efficacy and consumer appeal.

BRIEF SUMMARY

Disclosed herein are oral care compositions comprising at least one phosphate/acrylate copolymer, at least one cationic antibacterial agent such as cetylpyridinium chloride, and at least one surfactant. Also disclosed herein are oral care compositions comprising at least one phosphate/acrylate copolymer, at least one cationic antibacterial agent such as cetylpyridinium chloride, at least one synthetic anionic linear polycarboxylate, at least one surfactant, and at least one zinc salt.

In certain embodiments, the oral care compositions disclosed herein have a turbidity of less than or equal to 20 Nephelometric Turbidity Units at 25° C., such as less than or equal to 15 Nephelometric Turbidity Units at 25° C. In various embodiments of the disclosure, the at least one surfactant is a nonionic poly(oxyethylene)-poly(oxypropylene) block copolymer, and in various exemplary embodiments, the at least one surfactant is present in the oral care composition in an amount of about 1% by weight.

In certain embodiments, the at least one phosphate/acrylate copolymer is present in the oral care composition in an amount of at least about 2.5% by weight, such as about 2.5% by weight, and in certain exemplary embodiments, the at least one synthetic anionic linear polycarboxylate polymer is present in an amount of about 1% by weight. In various exemplary embodiments, the at least one cationic antibacterial agent is present in an amount ranging from about 0.03% to about 1.2% by weight, and in certain embodiments disclosed herein, the at least one zinc salt is present in an amount ranging from about 0.1% to about 0.5%.

Also disclosed herein are oral care compositions comprising at least one phosphate/acrylate copolymer present in an amount of about 2.5% by weight; cetylpyridinium chloride present in an amount of about 0.07% by weight; at least one synthetic anionic linear polycarboxylate polymer present in an amount of about 1% by weight; at least one surfactant; and zinc lactate. In certain embodiments of the oral care composition, the at least one surfactant is a nonionic poly(oxyethylene)-poly(oxypropylene) block copolymer, and in certain embodiments, the at least one surfactant is present in an amount ranging from about 0.1 to about 1% by weight.

Further disclosed herein are methods for the treatment and/or inhibition of gum disease or halitosis comprising contacting the oral cavity with an oral care composition comprising at least one phosphate/acrylate copolymer, at least one cationic antibacterial agent such as cetylpyridinium chloride, at least one synthetic anionic linear polycarboxylate, at least one surfactant, and at least one zinc salt.

Further disclosed herein are methods of making an oral care composition comprising at least one phosphate/acrylate copolymer, at least one cationic antibacterial agent such as cetylpyridinium chloride, at least one synthetic anionic linear polycarboxylate, at least one surfactant, and at least one zinc salt, said method comprising:
  (i) mixing water, the at least one surfactant, the at least one cationic antibacterial agent, the at least one zinc salt (such as zinc lactate), the synthetic anionic linear polycarboxylate polymer, and the phosphate/acrylate copolymer to form a main mix; and
  (ii) optionally mixing flavorants and/or cooling agents with a glycol to form a premix and adding the premix to the main mix after the main mix has been formulated.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

As used herein, the term "one or more of" with respect to a listing of items such as, for example, A and B, means A alone, B alone, or A and B. The term "at least one of" is used to mean one or more of the listed items can be selected.

Unless otherwise specified, all percentages and amounts expressed herein and elsewhere in the specification should be understood to refer to percentages by weight. The amounts given are based on the active weight of the material.

As used herein, an "oral care composition" refers to a composition for which the intended use can include oral care, oral hygiene, or oral appearance, or for which the intended method of use can comprise administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans.

Disclosed herein are oral care compositions, such as mouthwash compositions, comprising at least one phosphate/acrylate copolymer, at least one cationic antibacterial agent such as cetylpyridinium chloride, and at least one surfactant, such as a nonionic block copolymer. Also disclosed herein are oral care compositions comprising at least one phosphate/acrylate copolymer, at least one cationic antibacterial agent such as cetylpyridinium chloride, at least one surfactant, at least one synthetic anionic linear polycarboxylate, and at least one zinc salt such as zinc lactate.

Further disclosed herein are oral care compositions, such as mouthwash compositions, comprising at least one phosphate/acrylate copolymer present in an amount of at least about 2.5% by weight; at least one cationic antibacterial agent such as cetylpyridinium chloride present in an amount of less than about 0.1% by weight, such as about 0.07% by weight; at least one surfactant present in an amount of at least about 1% by weight, at least one synthetic anionic linear polycarboxylate present in an amount of at least about 1% by weight, and zinc lactate.

Phosphate/Acrylate Copolymer

As used herein, "phosphate/acrylate copolymer" refers to a polymer made up of acrylate monomers and phosphate-bearing monomers, such as a copolymerized product of a mixture of acrylic acid, methacrylic acid, and 2-hydroxyethyl methacrylate phosphates of Formula 1:

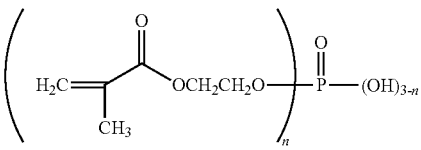

wherein n is 0, 1 or 2. In some embodiments, the phosphate/acrylate copolymer is a copolymerized product of a mixture of acrylic acid, methacrylic acid, and 2-hydroxyethyl methacrylate phosphates of Formula 1, comprising acrylic acid in a molar percentage of about 70-90%, about 80-90%, or about 85%; methacrylic acid in a molar percentage of about 5-20%, about 5-15%, or about 11%, and hydroxyethyl methacrylate phosphates of Formula 1 in a molar percentage of about 1-10%, about 2-6%, or about 4%. In some embodiments, the phosphate/acrylate copolymer has a weight average molecular weight of from about 10 to about 500 kDa, such as about 10 to about 200 kDa, about 10 to about 40 kDa, about 15 to about 25 kDa, or about 17 to about 23 kDa, and the phosphate/acrylate copolymer is below its glass transition temperature. In certain embodiments, the weight average molecular weight is about 10 to about 40 kDa. In other embodiments, the weight average molecular weight is about 17 to about 23 kDa. For example, in a particular embodiment, the phosphate/acrylate copolymer is a random copolymer that is the copolymerized product of a mixture of, in the relative amounts set forth in Table 1 below, 2-hydroxyethyl methacrylate phosphate, acrylic acid, and methacrylic acid.

TABLE 1

| Monomer Name and Structure | Monomer Weight Ratio (weight %) | Monomer Molar Ratio (Mole %) |
|---|---|---|
| 2-hydroxyethyl methacrylate phosphate<br>mixture of n = 0, n = 1, and n = 2 | 11 | 4 |
| acrylic acid | 75 | 85 |

TABLE 1-continued

| Monomer Name and Structure | Monomer Weight Ratio (weight %) | Monomer Molar Ratio (Mole %) |
| --- | --- | --- |
| methacrylic acid 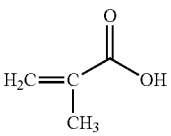 | 14 | 11 |

In certain embodiments, the phosphate/acrylate copolymers as described herein may include Mirapol DV8801 (Rhodia).

Provided herein is an oral care composition as follows: (1) comprising about 0.1 to about 10 weight % phosphate/acrylate copolymer, such as about 0.2 to about 9 weight % phosphate/acrylate copolymer, about 0.3 to about 8 weight % phosphate/acrylate copolymer, about 0.4 to about 7 weight % phosphate/acrylate copolymer, about 0.5 to about 6 weight % phosphate/acrylate copolymer, about 0.5 to about 5 weight % phosphate/acrylate copolymer, about 0.5 to about 4 weight % phosphate/acrylate copolymer, or about 0.5 to about 3 weight % phosphate/acrylate copolymer. In certain embodiments, provided herein is an oral care composition comprising at least about 2.5 weight % phosphate/acrylate copolymer, such as about 2.5 weight % phosphate/acrylate copolymer.

The phosphate side group of a phosphate/acrylate copolymer, as disclosed herein, may function as an anchor to deposit the copolymer onto the tooth surface, thereby forming a physical layer on the tooth surface that may inhibit staining and/or biofilm formation. Without being bound by theory, the copolymer may act by forming a barrier on the tooth surface, ultimately lowering the surface energy for bacterial attachment. The copolymer may also prevent bacteria from sticking together.

Cationic Antibacterial Agent

Cationic antibacterial agents that possess antibacterial activity (i.e., germicides) are used against bacteria and may be used in oral care compositions to counter plaque formation caused by bacteria in the oral cavity. In oral care compositions, this material may be highly effective in promoting oral hygiene by reducing the formation of dental plaque and calculus, which is generally accompanied by a reduction in periodontal diseases.

Among the most common of these cationic antibacterial agents are antiplaque quaternary ammonium compounds such as benzethonium chloride, diisobutylphenoxyethoxyethyl dimethyl benzyl ammonium chloride, and cetyl pyridinium chloride (CPC). Other cationic antibacterial quaternary ammonium compounds that may be mentioned include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, and quaternized 5-amino-1,3-bis(2-ethylhexyl)-5-methyl hexa hydro-pyrimidine may be mentioned as typical quaternary ammonium antibacterial agents. In certain exemplary embodiments disclosed herein, the at least one cationic antibacterial agent is CPC.

In certain embodiments, the antibacterial agent is included in the oral care composition in an amount of about 0.01 to about 1.5% by weight, such as about 0.03 to about 1.2% by weight. In certain embodiments disclosed herein, CPC is included in the oral care composition in an amount of about 0.01 to about 1.5% by weight, such as about 0.03 to about 1.2% by weight, or about 0.07% by weight.

Surfactants

In some embodiments, the oral care compositions disclosed herein may comprise at least one surfactant, such as surfactants selected from anionic, cationic, zwitterionic, and nonionic surfactants, and mixtures thereof. In some embodiments, the surfactant is reasonably stable throughout a wide pH range. In some embodiments, the oral care compositions disclosed herein may comprise from about 0.01 to about 10 weight % of a surfactant, such as about 0.05 to about 5 weight % of a surfactant, about 0.1 to about 10 weight % of a surfactant, about 0.1 to about 5 weight % of a surfactant, about 0.1 to about 2 weight % of a surfactant, or about 0.5 to about 2 weight % of a surfactant. In some embodiments, the oral care compositions disclosed herein may comprise from about 0.01 to about 10 weight % of a nonionic surfactant, such as about 0.05 to about 5 weight % of a nonionic surfactant, about 0.1 to about 10 weight % of a nonionic surfactant, about 0.1 to about 5 weight % of a nonionic surfactant, about 0.1 to about 2 weight % of a nonionic surfactant, about 0.4 to about 1 weight % of a nonionic surfactant, or about 1 weight % of a nonionic surfactant.

Non-ionic surfactants are known in the art and generally include surfactants that are not electrically charged. A preferred nonionic surfactant may be poly(oxyethylene)-poly(oxypropylene) block copolymers. Such copolymers are known commercially by the non-proprietary name of poloxamers. The name poloxamer is often used in conjunction with a numeric suffix to designate the individual identification of each copolymer. Poloxamers may have varying contents of ethylene oxide and propylene oxide which results in poloxamers that have a wide range of chemical structures and molecular weights. One poloxamer that may be mentioned is Poloxamer 407, sold under the trade name PLURONIC® F127 by BASF, Inc. (Parsippany, N.J.). In certain embodiments, the oral care compositions disclosed herein may comprise poloxamer as the at least one surfactant.

Anionic surfactants that may be used in the oral care compositions disclosed herein include, for example:
  (i) water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate;
  (ii) higher alkyl sulfates, such as sodium lauryl sulfate;

(iii) higher alkyl-ether sulfates, such as those of formula CH$_3$(CH$_2$)$_m$CH$_2$(OCH$_2$CH$_2$)$_n$OSO$_3$X, wherein m is 6-16, e.g., 10, n is 1-6, e.g., 2, 3 or 4, and X is Na or K, for example sodium laureth-2 sulfate (CH$_3$(CH$_2$)$_{10}$CH$_2$(OCH$_2$CH$_2$)OSO$_3$Na);

(iv) higher alkyl aryl sulfonates such as sodium dodecyl benzene sulfonate (sodium lauryl benzene sulfonate); and (v) higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

As used herein, "higher alkyl" refers to C$_{6-30}$ alkyl.

In some embodiments, the oral care compositions disclosed herein may comprise an anionic surfactant. In some embodiments, the anionic surfactant is the water soluble salt of alkyl sulfates having from 10 to 18 carbon atoms in the alkyl radical and water soluble salts of sulfonated monoglycerides of fatty acids having from 10 to 18 carbon atoms. Sodium lauryl sulfate, sodium lauroyl sarcosinate, and sodium coconut monoglyceride sulfonates are examples of anionic surfactants of that type. In some embodiments, the oral care compositions disclosed herein may comprise sodium lauryl sulfate, sodium ether lauryl sulfate, or a mixture thereof. In some embodiments, the oral care compositions disclosed herein may comprise sodium lauryl sulfate.

Anionic Linear Polycarboxylates

In various embodiments of the disclosure, the oral care compositions disclosed herein may comprise at least one synthetic anionic linear polycarboxylate. As used herein, "synthetic anionic linear polycarboxylate" refers to a polymer synthesized by using an olefinically or ethylenically unsaturated carboxylic acid that contains an activated carbon-to-carbon olefinic double bond and at least one carboxyl group. The acid contains an olefinic double bond that readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other olefinic monomers copolymerizable with such carboxylic monomers include vinyl acetate, vinyl chloride, dimethyl maleate and the like. The synthetic anionic linear polycarboxylate is mainly a hydrocarbon with optional halogen and O-containing substituents and linkages as present in for example ester, ether, and OH groups. The carboxyls may be in the form of the acid (—COOH) or carboxylate anion (—COO$^-$). The copolymers preferably contain sufficient carboxyl groups for water-solubility and adherence to plaque. The terms "synthetic" and "linear" do not include known thickening or gelling agents comprising carboxymethyl cellulose and other derivatives of cellulose and natural gums, nor Carbopols having reduced solubility due to cross-linkages.

In some embodiments, "synthetic anionic linear polycarboxylate" refers to 1:4 to 4:1 copolymers of maleic anhydride or acid with another polymerizable ethylenically unsaturated monomer, e.g., methyl vinyl ether (methoxyethylene), having a molecular weight (M.W.) of about 30,000 to about 2,500,000; for example 1:4 to 4:1, e.g., about 1:1, copolymers of methyl vinyl ether/maleic anhydride, e.g., in a ratio of about 1:1 substantially in an alternating sequence, wherein the anhydride is hydrolyzed following copolymerization to provide the corresponding acid, having a M.W. of about 30,000 to about 1,000,000, e.g. about 300,000 to about 800,000, e.g., as sold under the tradename GANTREZ®, e.g., GANTREZ© S-97 Pharmaceutical Grade (M.W. ca. 700,000), available from Ashland Specialty Chemicals, Bound Brook, N.J. 08805.

Zinc Salts

In various embodiments of the disclosure, the oral care compositions disclosed herein may comprise at least one zinc salt. In certain embodiments, the at least one zinc salt is a water-soluble zinc salt, such as zinc chloride or zinc lactate. Other exemplary zinc salts that may be mentioned include zinc oxide, zinc sulfate, zinc citrate, zinc gluconate, zinc malate, zinc tartrate, zinc carbonate, and zinc phosphate. In an exemplary embodiment, the oral care composition comprises zinc lactate. In some embodiments, the oral care compositions disclosed herein may comprise from about 0.01 to about 5 weight % of a zinc salt, such as about 0.05 to about 5 weight % of a zinc salt, about 0.05 to about 2 weight % of a zinc salt, about 0.1 to about 2 weight % of a zinc salt, about 0.1 to about 1 weight % of a zinc salt, or about 0.1 to about 0.5 weight % of a zinc salt. In certain exemplary embodiments, the oral care compositions disclosed herein may comprise from about 0.01 to about 5 weight % of zinc lactate, such as about 0.05 to about 5 weight % of zinc lactate, about 0.05 to about 2 weight % of zinc lactate, about 0.1 to about 2 weight % of zinc lactate, about 0.1 to about 1 weight % of zinc lactate, or about 0.1 to about 0.5 weight % of zinc lactate.

In further embodiments of the disclosure, the oral care compositions disclosed herein may comprise an orally acceptable carrier. As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a visual aid (e.g., a pigment, a dye, or a mixture thereof), an anti-caries agent, an anti-bacterial, a whitening agent, a desensitizing agent, a vitamin, a preservative, an enzyme, and mixtures thereof.

In some embodiments, the oral care compositions disclosed herein comprise water as the orally acceptable carrier. Water employed in the preparation of the oral care compositions disclosed herein may be deionized and free of organic impurities. Water may make up the balance of the oral care composition. In some embodiments, the oral care compositions disclosed herein may comprise 0 to about 90 weight % water, such as about 0.1 to about 90 weight % water, about 1 to about 80 weight % water, about 2 to about 70 weight % water, about 5 to about 60 weight % water, about 5 to about 50 weight % water, about 20 to about 60 weight % water, or about 10 to about 40 weight % water. This amount of water includes the free water that is added plus the amount that is introduced with other components of the oral care composition, such as with sorbitol.

As used herein, a "tartar control agent" refers to a compound or a mixture of compounds that inhibit the formation of tartar, a mixture of calcium phosphates on organic matrices, and/or the deposition of plaque on teeth to form tartar (calculus).

As used herein, "chemical stain" refers to a discoloration of a dental surface caused by adsorption or absorption of a colored agent on or into the surface, or caused by chemical reaction of material of the dental surface (e.g., dental enamel) with a colored or non-colored agent contacting the surface. "Chemical staining" herein means formation and/or development of a chemical stain.

As used herein, "dental surface" refers to a surface of a natural tooth or a hard surface of artificial dentition including a denture, dental plate, crown, cap, filling, bridge, dental implant and the like. In some embodiments, the dental surface is a natural tooth.

Biofilm comprises a diverse microbial community on the tooth surface embedded in a matrix of polymers of bacterial and salivary origin. Once a tooth surface is cleaned, a conditioning film of proteins and glycoproteins may be adsorbed rapidly to the tooth surface. Biofilm formation involves the interaction between early bacterial colonizers and this film. Subsequently, secondary colonizers adhere to the already attached early colonizers (co-aggregation), and this process contributes to the development of a matured biofilm. Inhibiting the growth of biofilm may involve preventing and minimizing the re-attachment of bacteria onto the tooth surfaces.

A thickener may provide a desirable consistency and/or stabilize and/or enhance performance (e.g., provide desirable active release characteristics upon use) of the oral care compositions disclosed herein. In some embodiments, the oral care compositions disclosed herein may comprise from about 0 to about 15 weight % of a thickener, such as about 0.1 to about 15 weight % of a thickener, about 0.1 to about 10 weight % of a thickener, about 0.1 to about 5 weight % of a thickener, about 0.5 to about 10 weight % of a thickener, about 0.5 to about 5 weight % of at a thickener, about 1 to about 4 weight % of a thickener, about 2 to about 5 weight % of a thickener, about 2 to about 4 weight % of a thickener, or about 3 to about 4 weight % of a thickener. Higher weight percentages may be used for chewing gums, lozenges and breath mints, sachets, non-abrasive gels and subgingival gels. Thickeners that may be used in the oral care compositions disclosed herein include, for example, carboxy vinyl polymers, carrageenan (also known as carrageenan gum), hydroxyethyl cellulose (HEC), natural and synthetic clays (e.g., Veegum and laponite), water soluble salts of cellulose ethers (e.g., sodium carboxymethylcellulose (CMC) and sodium carboxymethyl hydroxyethyl cellulose), natural gums (e.g., gum karaya, xanthan gum, gum arable, and gum tragacanth), colloidal magnesium aluminum silicate, silica (e.g., finely divided silica), polyvinyl pyrrolidone, carbowaxes, fatty acids and salts thereof, and mixtures thereof. In some embodiments, a mixture of thickening silica and carrageenan gum may be used as the thickener in the oral care compositions disclosed herein. In some embodiments, the oral care compositions disclosed herein comprise from about 0.01 to about 15 weight % of thickening silica and carrageenan gum, such as about 0.1 to about 1 weight % of thickening silica and carrageenan gum, about 0.1 to about 1.0 weight % of thickening silica and carrageenan gum, about 0.1 to about 5 weight % of thickening silica and carrageena gum, about 0.5 to about 10 weight % of thickening silica and carrageenan gum, about 0.5 to about 5 weight % of thickening silica and carrageenan gum, about 1 to about 4 weight % of thickening silica and carrageenan gum, about 2 to about 5 weight % of thickening silica and carrageenan gum, about 2 to about 4 weight % of thickening silica and carrageenan gum, or about 3 to about 4 weight % of thickening silica and carrageenan gum.

A buffer adjusts the pH of oral care compositions, for example, to a range of about pH 4.0 to about pH 6.0. In some embodiments, the oral care compositions disclosed herein may comprise from about 0.1 to about 10 weight % of a buffer, such as about 0.5 to about 10 weight % of a buffer, about 0.5 to about 5 weight % of a buffer, about 0.5 to about 4 weight % of a buffer, about 0.5 to about 3 weight % of a buffer, about 0.5 to about 2 weight % of a buffer, or about 1 to about 2 weight % of a buffer. Buffers that may be used in the oral care compositions disclosed herein include, for example, sodium bicarbonate, sodium phosphate {e.g., monosodium phosphate ($NaH_2PO_4$), disodium phosphate ($Na_2HPO_4$), and trisodium phosphate ($Na_3PO_4$)}, sodium hydroxide, sodium carbonate, sodium acid pyrophosphate, citric acid, sodium citrate, and mixtures thereof. In some embodiments, sodium hydroxide is used as the buffer in the oral care compositions disclosed herein. In some embodiments, the oral care compositions disclosed herein comprise from about 0.1 to about 10 weight % of sodium hydroxide, such as about 0.5 to about 10 weight % of sodium hydroxide, about 0.5 to about 5 weight % of sodium hydroxide, about 0.5 to about 4 weight % of sodium hydroxide, about 0.5 to about 3 weight % of sodium hydroxide, about 0.5 to about 2 weight % of sodium hydroxide, or about 1 to about 2 weight % of sodium hydroxide.

A humectant keeps oral care compositions from hardening upon exposure to air. Certain humectants can also impart desirable sweetness or flavor to oral care compositions. In some embodiments, the oral care compositions disclosed herein may comprise, on a pure humectant basis, from 0 to about 70 weight % of a humectant, such as about 10 to about 70 weight % of a humectant, about 10 to about 65 weight % of a humectant, about 10 to about 60 weight % of a humectant, about 10 to about 50 weight % of a humectant, about 20 to about 50 weight % of at a humectant, or about 20 to about 40 weight % of a humectant. Humectants that may be used in the oral care compositions disclosed herein include, for example, glycerin, sorbitol, xylitol, butylene glycol, polyethylene glycol, propylene glycol, trimethyl glycine, and mixtures thereof. In some embodiments, a mixture of glycerin, sorbitol, and propylene glycol is used as the humectant in the oral care compositions disclosed herein. In some embodiments, the oral care compositions disclosed herein may comprise, on a pure humectant basis, from 0 to about 70 weight % of glycerin, sorbitol, and propylene glycol, such as about 10 to about 70 weight % of glycerin, sorbitol, and propylene glycol, about 10 to about 65 weight % of glycerin, sorbitol, and propylene glycol, about 10 to about 60 weight % of glycerin, sorbitol, and propylene glycol, about 10 to about 50 weight % of glycerin, sorbitol, and propylene glycol, about 20 to about 50 weight % of glycerin, sorbitol, and propylene glycol, or about 20 to about 40 weight % of glycerin, sorbitol, and propylene glycol.

An abrasive removes debris and surface stains. In some embodiments, the oral care compositions disclosed herein may comprise about 5 to about 70 weight % of an abrasive, such as about 5 to about 60 weight % of an abrasive, about 5 to about 50 weight % of an abrasive, about 5 to about 40 weight % of an abrasive, about 5 to about 30 weight % of an abrasive, about 10 to about 30 weight % of an abrasive, or about 10 to about 20 weight % of an abrasive.

Abrasives that may be used in the oral care compositions disclosed herein include, for example, a calcium phosphate abrasive, e.g., tricalcium phosphate ($Ca_3(PO_4)_2$), hydroxyapatite ($Ca_{10}(PO_4)_6(OH)_2$), dicalcium phosphate dihydrate ($CaHPO_4 2H_2O$, also sometimes referred to as DiCal), calcium pyrophosphate, and mixtures thereof. Calcium carbonate, e.g., precipitated calcium carbonate, may also be employed as an abrasive.

Other abrasives that may be used in the oral care compositions disclosed herein include, for example, silica abrasives such as precipitated silicas having a mean particle size of up to about 20 microns, such as Zeodent® 115, marketed by J. M. Huber, as well as sodium metaphosphate, potassium metaphosphate, aluminum silicate, calcined alumina, bentonite or other siliceous materials, or mixtures thereof. Silica abrasives used herein, as well as the other abrasives, may have an average particle size ranging between about 0.1 and about 30 microns, such as between about 5 and about 15 microns. The silica abrasives may be from precipitated silica or silica gels, such as silica xerogels. Particular silica xerogels are marketed under the trade name Syloid® by the W. R. Grace & Co. Davison Chemical Division. Precipitated silica materials include those marketed by the J. M. Huber Corp, under the trade name Zeodent®, including the silica carrying the designation Zeodent® 115 and 119.

In some embodiments, abrasives that may be used in the oral care compositions disclosed herein include silica gels and precipitated amorphous silica having an oil absorption value of about less than about 100 cc/100 g silica and in the range of about 45 cc/100 g to about 70 cc/100 g silica. Oil absorption values are measured using the ASTA Rub-Out Method D281. In some embodiments, the silica comprises colloidal particles having an average particle size of about 3 microns to about 12 microns, such as about 5 to about 10 microns.

In some embodiments, the abrasive comprises a large fraction of very small particles, such as those having a d50 less than about 5 microns, e.g., small particle silica (SPS) having a d50 of about 3 to about 4 microns, e.g., Sorbosil AC43® (Ineos). Such small particles may be used in formulations targeted at reducing hypersensitivity. The small particle component may be present in combination with a second larger particle abrasive.

Low oil absorption silica abrasives that may be used in the oral care compositions disclosed herein are marketed under the trade designation Sylodent® WXA by Davison Chemical Division of W.R. Grace & Co., Baltimore, Md. 21203. Sylodent® 650 XWA, a silica hydrogel composed of particles of colloidal silica having a water content of about 29% by weight averaging about 7 to about 10 microns in diameter, and an oil absorption of less than about 70 cc/100 g of silica is an example of a low oil absorption silica abrasive that may be used in the oral care compositions disclosed herein.

In some embodiments, the oral care compositions disclosed herein may comprise a high cleaning silica. In some embodiments, the oral care compositions disclosed herein may comprise about 5 to about 70 weight % high cleaning silica, such as about 5 to about 60 weight % high cleaning silica, about 5 to about 50 weight % high cleaning silica, about 5 to about 40 weight % high cleaning silica, about 5 to about 30 weight % high cleaning silica, about 10 to about 30 weight % high cleaning silica, or about 10 to about 20 weight % high cleaning silica.

In some embodiments, the oral care compositions disclosed herein may comprise a sweetener. In some embodiments, the oral care compositions disclosed herein may comprise about 0.002 to about 10 weight % of a sweetener, such as about 0.002 to about 10 weight % of a sweetener, about 0.01 to about 5 weight % of a sweetener, about 0.01 to about 3 weight % of a sweetener, about 0.01 to about 1 weight % of a sweetener, or about 0.01 to about 0.05 weight % of a sweetener. Sweeteners that may be used in the oral care compositions disclosed herein include, for example, sucrose, glucose, saccharin, sucralose, dextrose, levulose, lactose, mannitol, sorbitol, fructose, maltose, xylitol, saccharin salts (such as sodium saccharin), thaumatin, aspartame, D-tryptophan, dihydrochalcones, acesulfame, cyclamate salts, and mixtures thereof. In some embodiments, sodium saccharin is used as the sweetener in the oral care compositions disclosed herein. In some embodiments, the oral care compositions disclosed herein comprise about 0.005 to about 10 weight % sodium saccharin, such as about 0.01 to about 10 weight % sodium saccharin, about from 0.01 to about 5 weight % sodium saccharin, about from 0.01 to about 3 weight % sodium saccharin, about 0.01 to about 1 weight % sodium saccharin, or about 0.01 to about 0.05 weight % sodium saccharin.

In some embodiments, the oral care compositions disclosed herein may comprise at least one flavorant. In some embodiments, the oral care compositions disclosed herein may comprise about 0.01 to about 5 weight % of a flavorant, such as about 0.01 to about 4 weight % of a flavorant, about 0.01 to about 3 weight % of a flavorant, about 0.01 to about 2 weight % of a flavorant, or about 0.02 to about 2 weight % of a flavorant. Flavorants that may be used in the oral care compositions disclosed herein include, for example, essential oils, as well as various flavoring aldehydes, esters, alcohols, and similar materials, as well as menthol, carvone, and anethole, as well as mixtures thereof. Examples of essential oils include oils of spearmint, peppermint, wintergreen, sassafras, clove, sage, eucalyptus, marjoram, cinnamon, lemon, lime, grapefruit, and orange. In some embodiments, a mixture of peppermint oil and spearmint oil is used as the flavorant in the oral care compositions disclosed herein.

In some embodiments, the oral care compositions disclosed herein may comprise at least one visual aid, including but not limited to pigments, dyes, speckles, beads, strips, and mixtures thereof. In some embodiments, the oral care compositions disclosed herein comprise about 0.0001 to about 20 weight % of a visual aid, such as about 0.0001 to about 10 weight % of a visual aid, about 0.0001 to about 5 weight % of a visual aid, about 0.0001 to about 3 weight % of a visual aid, or about 0.0001 to about 0.1 weight % of a visual aid. In some embodiments, the oral care compositions disclosed herein comprise titanium dioxide, such as about 0.1 to about 1 weight % titanium dioxide.

In some embodiments, the oral care compositions disclosed herein may further comprise an anti-caries agent. In some embodiments, the oral care compositions disclosed herein comprise about 0.005 to about 10 weight % of the anti-caries agent, such as about 0.01 to about 10 weight % of the anti-caries agent, about 0.01 to about 5 weight % of the anti-caries agent, about 0.01 to about 1 weight % of the anti-caries agent, about 0.01 to about 0.3 weight % of the anti-caries agent, about 0.1 to about 10 weight % of the anti-caries agent, about 0.1 to about 5 weight % of the anti-caries agent, about 0.1 to about 2 weight % of the anti-caries agent, about 0.1 to about 1 weight % of the anti-caries agent, about 0.1 to about 0.8 weight % of the anti-caries agent, about 0.1 to about 0.6 weight % of the anti-caries agent, or about 0.1 to about 0.5 weight % of the anti-caries agent. In some embodiments, the anti-caries agent is a fluoride ion source. In some embodiments, the oral care compositions disclosed herein further comprises about 0.005 to about 10 weight % of the anti-caries agent which is a fluoride ion source, such as about 0.01 to about 10 weight % of the anti-caries agent which is a fluoride ion source, about 0.01 to about 5 weight % of the anti-caries agent which is a fluoride ion source, about 0.01 to about 1 weight % of the anti-caries agent which is a fluoride ion source, about 0.01 to about 0.3 weight % of the anti-caries agent which is a fluoride ion source, about 0.1 to about 10 weight % of the anti-caries agent which is a fluoride ion source, about 0.1 to about 5 weight % of the anti-caries agent which is a fluoride ion source, about 0.1 to about 2 weight % of the anti-caries agent which is a fluoride ion source, about 0.1 to about 1 weight % of the anti-caries agent which is a fluoride ion source, about 0.1 to about 0.8 weight % of the anti-caries agent which is a fluoride ion source, about 0.1 to about 0.6 weight % of the anti-caries agent which is a fluoride ion source, or about 0.1 to about 0.5 weight % of the anti-caries agent which is a fluoride ion source. Examples of fluoride ion sources that may be used in the oral compositions disclosed herein include, for example, stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof. In certain embodiments the fluoride ion source includes stannous fluoride, sodium fluoride, and sodium monofluorophosphate, as well as mixtures thereof. In some embodiments, the anti-caries agent is sodium fluoride. In some embodiments, the oral care compositions disclosed herein comprise about 0.005 to about 10 weight % sodium fluoride, such as about 0.01 to about 10 weight % sodium fluoride, about 0.01 to about 5 weight % sodium fluoride, about 0.01 to about 1 weight % sodium fluoride, about 0.01 to about 0.3 weight % sodium fluoride, about 0.1 to about 10 weight % sodium fluoride, about 0.1 to about 5 weight % sodium fluoride, about 0.1 to about 2 weight % sodium fluoride, about 0.1 to about 1 weight % sodium fluoride, about 0.1 to about 0.8 weight % sodium fluoride, about 0.1 to about 0.6 weight % sodium fluoride, or about 0.1 to about 0.5 weight % sodium fluoride.

In some embodiments, the oral care compositions disclosed herein comprise the anti-caries agent which is a fluoride ion source in an amount sufficient to supply about 25 ppm to about 25,000 ppm of fluoride ions, such as from about 100 to about 20,000 ppm of fluoride ions, from about 300 to about 15,000 ppm of fluoride ions, from about 500 to about 10,000 ppm of fluoride ions, from about 500 to about 8,000 ppm of fluoride ions, from 500 to about 6,000 ppm of fluoride ions, from about 500 to about 4,000 ppm of fluoride ions, from about 500 to about 2,000 ppm of fluoride ions, from about 500 to about 1,800 ppm of fluoride ions, from about 1,000 to about 1,600 ppm, or about 1,450 ppm of fluoride ions. The appropriate level of fluoride ions will depend on the particular application. In some embodiments, a toothpaste for consumer use comprises the anti-caries agent which is a fluoride ion source in an amount sufficient to supply from about 1,000 to about 1,500 ppm of fluoride ions, with pediatric toothpaste having somewhat less. In some embodiments, a dentifrice or coating for professional application comprises the anti-caries agent which is a fluoride ion source in an amount sufficient to supply from about 5,000 to about 25,000 ppm of fluoride ions.

In some embodiments, the oral care compositions disclosed herein may comprise an additional anti-bacterial or anti-attachment agent. In some embodiments, the oral care compositions disclosed herein, may comprise about 0.01 to about 10 weight % of an additional anti-bacterial agent, such as about 0.1 to about 10 weight %, about 0.5 to about 5 weight %, about 0.01 to about 5 weight %, about 0.05 to about 4 weight %, about 0.05 to about 3 weight %, about 0.05 to about 2 weight %, about 0.05 to 1 weight %, about 0.1 to about 1 weight %, or about 0.1 to about 0.5 weight %. The amount of the additional anti-bacterial will vary depending on the type of oral care composition, with levels used in toothpaste being, for example, 5 to 15 times greater than used in a mouthwash. For example, a mouthwash comprising triclosan may comprise, for example, about 0.03 weight % triclosan while a toothpaste comprising triclosan may comprise about 0.3 weight % triclosan. Examples of additional anti-bacterials that may be used in the oral compositions disclosed herein, may include, for example, halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts, methyl hydroxybenzoate, and mixtures thereof.

A whitening agent whitens a tooth to which it is applied. In some embodiments, the oral care compositions disclosed herein may comprise at least one whitening agent. In some embodiments, the oral care compositions disclosed herein may comprise a whitening agent in a dental surface-whitening effective amount, such as about 0.1 to about 90 weight %, about 0.5 to about 50 weight %, about 1 to about 30 weight %, or about 2 to about 10 weight %. Examples of whitening agents that may be used in the oral compositions disclosed herein may include, for example, peroxides, metal chlorites, perborates, percarbonates, peroxyacids, hypochlorites, and mixtures thereof. In some embodiments, the whitening agent is hydrogen peroxide or a hydrogen peroxide source, for example, urea peroxide or a peroxide salt or complex (for example, peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or a hydrogen peroxide polymer complex (for example, a peroxide-polyvinyl pyrrolidone polymer complex).

In certain embodiments, the oral care compositions disclosed herein may be clear, translucent, or transparent. Clarity may be considered a characteristic of stability, and in certain embodiments, the clarity of a stable composition may be maintained for lengthy periods of time. For example, clarity of the finished composition may, in certain embodiments, be maintained for a period of at least one month, such as at least two months or at least three months.

Stability of a mouthwash composition may, in certain embodiments, be measured based on the composition's turbidity/clarity. Turbidity is the cloudiness or haziness of a fluid caused by individual particles (i.e., suspended solids) that are generally invisible to the naked eye. The measurement of turbidity may be used as a test of mouthwash cosmetic acceptability for consumer use. The units of turbidity from a calibrated nephelometer are called Nephelometric Turbidity Units (NTU). Acceptable turbidity measurements taken using a Hach turbidity meter may, in certain embodiments, range from about 0 to about 20 NTU at 25° C. The clarity may also be evaluated visually in certain instances. In certain embodiments, an acceptable turbidity may be less than or equal to about 25 NTU, such as less than or equal to about 20 NTU, or less than or equal to about 15 NTU at 25° C.

Further provided herein are methods for the treatment and/or inhibition of a chemical slain, plaque, and/or tartar on a dental surface, comprising contacting the dental surface with the oral care compositions disclosed herein. Also provided herein is the use of the oral care compositions disclosed herein for the treatment and/or inhibition of a chemical stain, plaque, and/or tartar on a dental surface.

Also provided herein are methods for the treatment and/or inhibition of gum disease or halitosis comprising contacting the oral cavity with the oral care compositions disclosed herein. In certain embodiments, gum disease may be gingivitis or periodontitis. Also provided herein is the use of the oral care compositions disclosed herein for the treatment and/or inhibition of gum disease or halitosis.

Further provided herein are methods for inhibiting biofilm formation on a dental surface comprising contacting the dental surface with the oral care compositions disclosed herein. Also provided herein is the use of the oral care compositions disclosed herein for inhibiting biofilm formation on a dental surface.

Further provided are methods for treating and/or inhibiting bacteria from sticking together and growing into bigger colonies in an oral cavity comprising contacting the oral cavity with the oral care compositions disclosed herein. Also disclosed herein is the use of the oral care compositions disclosed herein for treating and/or inhibiting bacteria from sticking together and growing into bigger colonies in an oral cavity.

As used herein, "inhibition" refers to reduction of stains, bacteria, biofilm, gum disease, halitosis, and the like that would otherwise form or develop subsequent to the time of the treatment. Such inhibition can range from a small but observable or measurable reduction to complete inhibition of subsequent staining, bacteria growth, biofilm formation, gum disease formation, halitosis formation, or the further growth or progression of any of the foregoing, by comparison with an untreated or placebo-treated dental surface.

With respect to staining, where the dental surface is substantially free of chemical stains, the methods and uses disclosed herein may be effective to inhibit formation and development of new chemical stains, as can occur for example by oral use of tobacco products (including smoking) or by drinking tea, coffee, red wine, or soda, subsequent to treatment according to the method. Where the dental surface already possesses some degree of chemical staining, the methods and uses disclosed herein may be effective to inhibit further development of the existing stain. In some embodiments, the methods and uses disclosed herein can remove, partially or completely, an existing chemical stain as well as inhibit subsequent staining.

Also provided here are methods of making the oral care compositions disclosed herein as a mouthwash that includes the at least one phosphate/acrylate copolymer and at least one cationic antibacterial agent, as well as the at least one synthetic anionic linear polycarboxylate polymer, the at least one surfactant, and at least one zinc salt, such as zinc lactate. The method can form a composition that may be both stable and transparent. In certain embodiments, the method comprises the following steps:

(i) mixing water, at least one surfactant, at least one cationic antibacterial agent, at least one zinc salt (such as zinc lactate), synthetic anionic linear polycarboxylate polymer, and phosphate/acrylate copolymer to form a main mix; and (ii) optionally mixing flavorants and/or cooling agents with a glycol to form a premix and adding the premix to the main mix after the main mix has been formulated.

The method may further comprise the addition of any other ingredients, such as sweeteners or a fluoride source, during step (i) by adding the additional ingredients to the main mix.

Any additional materials, such as sweeteners, fluoride, colorants, and preservatives can be added to the main mix prior to the premixes being added.

EXAMPLES

Example 1

Three mouthwash formulations were prepared as described below in Table 1, comprising varying quantities of cetylpyridinium chloride, phosphate/acrylate copolymer, synthetic anionic linear polycarboxylate, and surfactant.

TABLE 1

| Ingredient | Formulation A | Formulation B | Formulation C |
|---|---|---|---|
| Cetylpyridinium chloride | 0.1% | 0.1% | 0.07% |
| Zinc lactate | 0.28% | 0.28% | 0.28% |
| phosphate/acrylate copolymer | 2.5% | 1.25% | 2.5% |
| Gantrez ® | 1% | 0.45% | 1% |
| Pluronic ® F127 | 0.4% | 0.67% | 1% |
| Potassium sorbate | 0.1% | 0.1% | 0.1% |
| Sodium fluoride | — | — | 0.05% |
| Glycerin | 7.5% | 7.5% | 7.5% |
| Sorbitol | 5.5% | 5.5% | 5.5% |
| Propylene glycol | 8% | 8% | 8% |
| Water, sweeteners, flavorants | QS | QS | QS |

The formulations prepared in Table 1 were then measured for turbidity using a Hach turbidity meter. It is noted that, although Formulations A and B contained 2.5% and 1.25% of phosphate/acrylate copolymer, respectively, it is believed that similar formulations comprising a range of 0 to 2.5% phosphate/acrylate copolymer (for Formulation A) and 0 to 1.25% (for Formulation B) would yield similar results. Table 2 below details the results obtained for the formulations prepared.

TABLE 2

Hach Turbidity Meter Data

| Formulations | Turbidity Measurement at 25° C. (NTU) |
|---|---|
| A | 64.8 |
| B | 22.7 |
| C | 14.5 |

As can be seen from Table 2, Formulation C has a low turbidity (i.e., less than 20 NTU), and is thus considered a cosmetically stable and consumer acceptable formulation for a mouthwash composition.

Example 2

The stability of Formulation C was evaluated over time and under accelerated aging conditions (temperature and relative humidity). Table 3 below details the conditions and results. As can be seen from Table 3, Formulation C was considered stable, as it retained a clear color/appearance, over time and at varying temperatures and relative humidity.

TABLE 3

Cosmetic Stability of Formulation C

| Condition | Time | # of Pulls | pH (as is) | Color/appearance | CPC |
|---|---|---|---|---|---|
| −10° C. | 1 mo | 1 | — | Clear | — |
| −10° C. | 2 mo | 1 | — | Clear | — |
| −10° C. | 3 mo | 1 | — | White floating particles on top, which went away after 24 hrs vigorous shaking, leading to clear solution | — |
| −30° C. | 1 mo | 1 | — | Clear | — |
| −30° C. | 2 mo | 1 | — | Clear | — |
| −30° C. | 3 mo | 1 | — | Clear | — |
| 25° C./60% RH | 0 mo | 10 | 6.6 | Clear, Pass | 0.07% |
| 25° C./60% RH | 1 mo | 6 | 6.49 | Clear | 0.07% |
| 25° C./60% RH | 2 mo | 6 | 6.52 | Clear | 0.07% |
| 25° C./60% RH | 3 mo | 6 | 6.53 | Clear | 0.07% |
| 40° C./75% RH | 1 mo | 6 | 6.54 | Clear | 0.07% |
| 40° C./75% RH | 2 mo | 7 | 6.52 | Clear | 0.07% |
| 40° C./75% RH | 3 mo | 7 | 6.57 | Clear, slightly tinted | 0.07% |
| 49° C. | 1 mo | 1 | — | Clear, slightly tinted color | — |
| 49° C. | 2 mo | 1 | — | Clear, tinted color | — |
| 49° C. | 3 mo | 1 | — | Clear, tinted | — |
| 4° C. | 1 mo | 1 | — | Clear | — |
| 4° C. | 2 mo | 1 | — | Clear | — |
| 4° C. | 3 mo | 1 | — | Clear | — |
| freeze/thaw cycle | 1 day | 1 | — | Clear, Pass | — |
| freeze/thaw cycle | 3 days | 1 | — | Clear, Pass | — |
| freeze/thaw cycle | 5 days | 6 | 6.5 | Clear, Pass | 0.07% |

Example 3

Formulation C was tested for its ability to prevent stains on tooth surfaces.

Bovine enamel substrates were prepared and subjected to clarified saliva for a period of about an hour until a pellicle forms over the substrate. The substrates are blotted dry and absorbance is measured on a CM-700d Spectrophotometer colorimeter, sold by Konica Minolta Sensing Americas, located at 101 Williams Drive Ramsey, N.J. 07446. The substrates are treated with one of Formulation C, a Commercial Example or a control of deionized water. The Commercial Example is defined below in Table 4.

TABLE 4

Commercial Example

| Ingredient | Concentration (wt. %) |
|---|---|
| Humectant | 15-20 |
| Gantrez ® | 1 |
| Tetrapotassium pyrophosphate | 1.35 |
| Tetrasodium pyrophosphate | 0.45 |
| Zinc citrate | 0.28 |
| Preservative | 1 |
| Colors, Flavorants, Sweeteners | 0.01-1 |
| Sodium fluoride | 0.05 |
| Water | q.s. |

The substrates are subsequently incubated in water at 37° C. for 5 minutes. The substrates are rinsed twice with deionized water and absorbance is once again measured using the colorimeter. Each substrate is then exposed to a stain solution and subsequently incubated in water at 37° C. for 15 minutes. The substrates are once again subjected to clarified saliva and incubated in water at 37° C. for 20 minutes. This process is repeated for two more cycles. After three staining cycles, the absorbance of the substrates is measured and the overall change is color ($\Delta E$) is plotted. The table below summarizes the results.

TABLE 5

Change of color calculated as a measure of $\Delta E$

| Substrate | Product Tested | $\Delta E$ |
|---|---|---|
| 1 | Formulation C | 17.05 |
| 2 | Commercial Example | 20.24 |
| 3 | Deionized Water | 28.77 |

As clearly shown above, when substrates are treated with Formulation C prior to being subjected to multiple staining cycles, they show the least overall change in color when compared with controls. The Commercial Example, which is a product specializing in preventing and removing surface stains on teeth, showed reduced color change in comparison to the water control (Substrate 3), but still did not prevent stains to the same degree as Formulation C. In fact, formulation C showed about a 16% improvement in prevention of surface stains over the Commercial Example.

While the present invention has been described with reference to embodiments, it will be understood by those skilled in the art that various modifications and variations may be made therein without departing from the scope of the present invention as defined by the appended claims.

What is claimed is:

1. An oral care composition comprising:
   at least one phosphate/acrylate copolymer in an amount of from 2.5% to 4% by weight;
   at least one cationic antibacterial agent in an amount of greater than 0.03% and less than 0.1% by weight;
   at least one synthetic anionic linear polycarboxylate polymer in an amount of at least 1% by weight;
   at least one surfactant in an amount of from 1% to 2% by weight; and
   zinc lactate in an amount ranging from 0.1% to 0.5% by weight,
   wherein the at least one surfactant is a nonionic poly(oxyethylene)-poly(oxypropylene) block copolymer, and wherein the at least one cationic antibacterial agent is cetylpyridinium chloride, and wherein the at least one phosphate/acrylate co-polymer is a co-polymerized product of acrylic acid, methacrylic acid, and a mixture of 2-hydroxyethyl methacrylate phosphates of Formula 1:

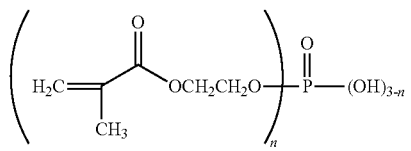

wherein n is 0, 1 and 2;

wherein the oral care composition has a turbidity of less than or equal to 15 Nephelometric Turbidity Units at 25° C.

2. The oral care composition according to claim 1, wherein the at least one phosphate/acrylate copolymer is present in an amount of about 2.5% by weight.

3. The oral care composition according to claim 1, wherein the at least one synthetic anionic linear polycarboxylate polymer is present in an amount of about 1% by weight.

4. The oral care composition according to claim 1, wherein the at least one cationic antibacterial agent is present in an amount of about 0.07% by weight.

5. The oral care composition according to claim 1, wherein the at least one surfactant is present in an amount of about 1% by weight.

6. The oral care composition according to claim 1, wherein the zinc lactate is present in an amount of 0.28% by weight.

7. An oral care composition comprising:
   at least one phosphate/acrylate copolymer present in an amount of about 2.5% by weight;
   cetylpyridinium chloride present in an amount of about 0.07% by weight;
   at least one synthetic anionic linear polycarboxylate polymer present in an amount of about 1% by weight;
   at least one surfactant in an amount of from 1% to 2% by weight; and
   zinc lactate in an amount ranging from 0.1% to 0.5% by weight, wherein the at least one surfactant is a nonionic poly(oxyethylene)-poly(oxypropylene) block copolymer, and wherein the at least one phosphate/acrylate co-polymer is a co-polymerized product of acrylic acid, methacrylic acid, and a mixture of 2-hydroxyethyl methacrylate phosphates of Formula 1:

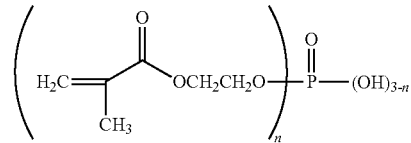

wherein n is 0, 1 and 2;

wherein the oral care composition has a turbidity of less than or equal to 15 Nephelometric Turbidity Units at 25° C.

8. The oral care composition according to claim 7, wherein the at least one surfactant is present in an amount of about 1% by weight.

9. A method for the treatment and/or inhibition of gum disease or halitosis comprising contacting the oral cavity with an oral care composition according to claim 1.

10. A method of making the oral care composition of claim 1, comprising:
   (i) mixing water, the at least one surfactant, the at least one cationic antibacterial agent, the zinc lactate, the synthetic anionic linear polycarboxylate polymer, and the phosphate/acrylate copolymer to form a main mix; and
   (ii) optionally mixing flavorants and/or cooling agents with a glycol to form a premix and adding the premix to the main mix after the main mix has been formulated.

11. The oral care composition according to claim 1, wherein the composition is a mouthwash.

12. The oral care composition according to claim 7, wherein the zinc lactate is present in an amount of 0.28% by weight.

13. The oral care composition according to claim 7, wherein the composition is a mouthwash.

* * * * *